(12) United States Patent
Nishikawa et al.

(10) Patent No.: US 6,306,907 B1
(45) Date of Patent: Oct. 23, 2001

(54) ANTIPSYCHOTIC

(75) Inventors: Masazumi Nishikawa; Shoji Kimura, both of Tsukuba (JP)

(73) Assignee: Taiyo Fishery Co., Ltd., Tokyo (JP)

( * ) Notice: Subject to any disclaimer, the term of this patent is extended or adjusted under 35 U.S.C. 154(b) by 0 days.

(21) Appl. No.: 08/111,831

(22) Filed: Aug. 25, 1993

(30) Foreign Application Priority Data

Aug. 26, 1992 (JP) .................................................. 4-227510

(51) Int. Cl.$^7$ ................................................. A61K 31/20
(52) U.S. Cl. ................................................................ 514/558
(58) Field of Search ............................................ 514/558

(56) References Cited

U.S. PATENT DOCUMENTS

| | | | | |
|---|---|---|---|---|
| 5,112,863 | * | 5/1992 | Hashimoto et al. | 514/534 |
| 5,120,760 | * | 6/1992 | Horrobin | 514/458 |
| 5,260,067 | * | 11/1993 | Zheng | 424/450 |

OTHER PUBLICATIONS

HCAPLUS abstract, AN 1989:457336, VanRollins, M. et al., J. Lipid. Res. (1989), 30(2), pp. 275–286.*
Goodman Gilman, A. et al., "The Pharmacological Basis of Therapeutics" (6$^{th}$ Ed.), Macmillan Pub. Co., New York, (1980), p. 12.*
HCAPLUS abstract, AN 1984: 419194, VanRollins, M. et al., J. Biol. Chem. (1984), 259(9), pp. 5776–5783.*
Chemical Abstracts 113: 158684, Horrobin, (1989).*
Chemical Abstracts 112: 191978, Kimura et al., (1989).*
Chemical Abstracts 119: 125193 (1991), Nishikawa et al.*
Chemical Abstract 113: 71343 (1989), Kimura et al.*
Goodman Gilman et al. (Eds.), The Pharmacological Basis of Therapeutics, 6$^{th}$ Ed., Macmillan Pub. Co., New York, 1980, pp. 14–15 and 670–671.*

* cited by examiner

*Primary Examiner*—Russell Travers
*Assistant Examiner*—Shengiun Wang
(74) *Attorney, Agent, or Firm*—Finnegan, Henderson, Farabow, Garrett & Dunner, L.L.P.

(57) ABSTRACT

An antipsychotic comprising at least one of docosahexaenoic acid or derivatives thereof as an active ingredient.

An antipsychotic is provided which is effective in treating or preventing psychosis and which is highly safe.

7 Claims, 2 Drawing Sheets

ANTIPSYCHOTIC

This application claims foreign priority of JP 227510/1992, filed Aug. 26, 1992.

BACKGROUND OF THE INVENTION

The present invention relates to an antipsychotic.

Psychosis is a mental disease characterized by, for example, schizophrenia and its symptoms can be classified into two types, positive symptoms such as hallucinations, delusions, and abnormal behaviors and negative symptoms such as catatonia, autism, and non-emphasis. Chlorpromazine phenothiazine derivative produced in 1952 was the first antipsychotic to be developed. Haloperidol developed in 1963 is one of the most representative antipsychotics. However, these antipsychotics mainly function to improve positive symptoms caused by blockage of dopamine receptors but are ineffective in improving negative symptoms which are believed to be basic to the schizophrenia pattern. In addition, phencyclidine, an arylcyclohexyl amine derivative, is frequently being abused today by drug users in America and the resulting rapid increase in the number of patients showing schizophrenia-like symptoms has become a social problem. Since such patients show not only positive symptoms of schizophrenia but also its negative symptoms, there is a need for a drug which can improve not only positive symptoms of schizophrenia but also its negative symptoms and which causes no side effect.

SUMMARY OF THE INVENTION

Accordingly, an object of the present invention is to provide an antipsychotic which is effective in treating or preventing psychosis and which causes few or no side effects.

DESCRIPTION OF THE INVENTION

Figure 1A:
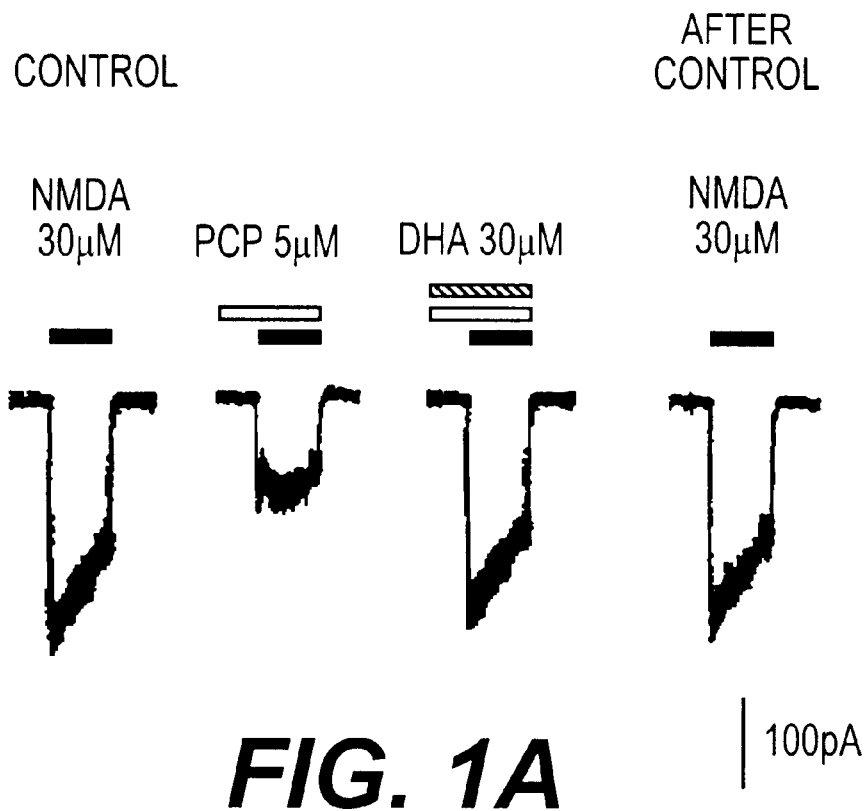
FIG. 1 is a graph showing the results of the tests on neurons by an electrophysiological procedure.
Figure 1B:
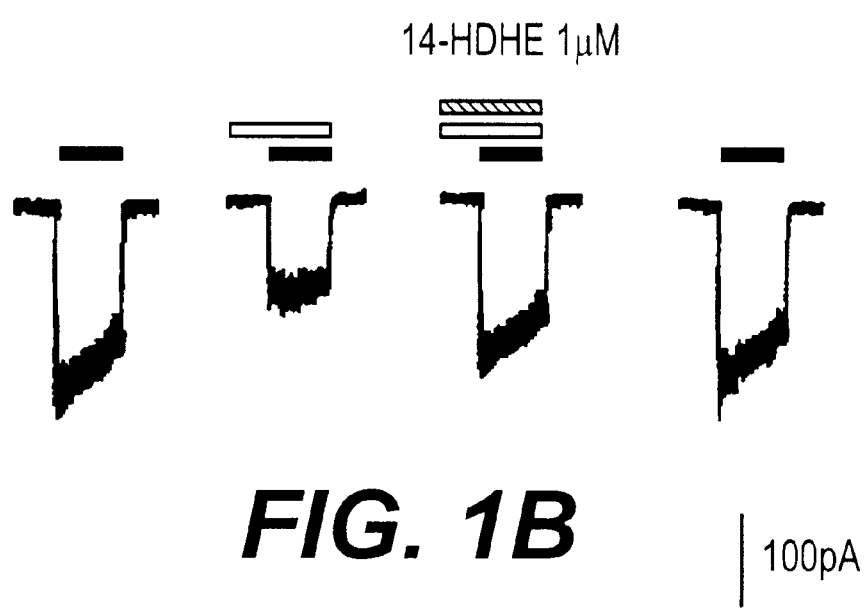
Figure 1C:

The inventors have conducted various studies on the physiological activities and pharmaceutical activities of docosahexaenoic acid which is contained in large amounts in the oil of sardines and sauries and have found that this compound and derivatives thereof have shown an unexpectedly strong antipsychotic action or psychosis-preventive action in animal tests and in several basic clinical tests. These compounds occur naturally both in animals such as fish and also in plants. Furthermore, the presence of these compounds in the central nervous systems of mammals including human beings has been confirmed and they are highly estimated for safety.

According to the present invention, there is provided an antipsychotic comprising at least one of docosahexaenoic acid and derivatives thereof as an active ingredient.

The inventors have found experimentally that docosahexaenoic acid or derivatives thereof are pharmaceutically effective in treating or preventing psychosis, and have consequently developed a drug utilizing the pharmaceutical effects of these compounds.

The inventors have studied the action of docosahexaenoic acid on the central nervous system at both a behavior and cellular level. In behavioral studies, it was confirmed that docosahexaenoic acid is effective in reducing the duration of tonic convulsion induced by maximum electroshock convulsions. In addition, it has been confirmed that docosahexaenoic acid acts to improve brain function, increasing learning ability and increasing memory capacity, and exhibits an antidementia action. Patent applications were subsequently filed (Japanese Unexamined Patent Application Nos. 279827/89 and 49723/90). At a cellular level, docosahexaenoic acid directly activates protein kinase C (C kinase, hereinafter referred to as "PKC") which is similar to arachidonic acid. It is believed that the activation of PKC is associated with synapse plasticity and with high efficiency of synaptic transmission, that is, long-term enhancement, thereby improving the brain functions. Furthermore, as will be shown in Example 1, it has been verified that docosahexaenoic acid regulates the function of N-methyl-D-aspartic acid (hereinafter referred to as "NMDA") receptors, which are glutamic acid receptors and reduces NMDA receptor antagonistic action of phencyclidine (hereinafter referred to as "PCP"), as a result, it had become clear that docosahexaenoic acid is an effective anti-psychotic agent.

The present invention will be hereinafter explained in detail.

The derivatives of docosahexaenoic acid that can be used in the present invention include fatty acids, phospholipids, or triglycerides; salts, amides, or esters; lipoxygenase metabolites or derivatives thereof; and P450 dehydrogenase metabolites or derivatives thereof. Examples of the esters include esters obtained by alcoholysis of docosahexaenoic acid, such as methyl and ethyl esters of docosahexaenoic acid. Examples of the lipoxygenase metabolites include 14-hydroxy docosahexaenoic acid and 7-hydroxy docosahexaenoic acid. Examples of derivatives of lipoxygenase metabolites include methyl 14-hydroxy docosahexaenoate and ethyl 7-hydroxy docosahexaenoate. Examples of the P450 dehydrogenase metabolites include 7,8-epoxy docosapentaenoic acid. Examples of derivatives of P450 dehydrogenase metabolites include ethyl 7,8-epoxy docosapentaenoate.

Docosahexaenoic acid or derivatives thereof that can be used in the present invention may typically be prepared by the following procedure:

Sardine oil as a raw material is saponified to form a fatty acid, which is then subjected to alcoholysis to give an ethyl ester. The ethyl ester may be separated and purified on molecular distillation equipment to yield ethyl docosahexaenoate having a high purity. Docosahexaenoic acid can be obtained by another saponification of the ester.

When docosahexaenoic acid or derivatives thereof are clinically used as antipsychotics, these compounds used as active ingredients are preferably formulated with solid or liquid pharmaceutical carriers, or diluents (vehicles), and additives such as stabilizers. In the pharmaceutical formulation, the ratio of the active ingredient to the carrier ingredient can be varied between 1 and 90% by weight. The formulation may be administered by the oral route, either in various dosage forms such as granules, subtilized granules, powders, tablets, capsules, pills, or a solution, or directly as bulk powders or liquids. Alternatively, the formulation may be administered as an injection by an intravenous, intramuscular, or subcutaneous route.

Any organic or inorganic, solid or liquid pharmaceutical carriers or diluents suitable for oral, enteral, or parenteral administration can be used to prepare the antipsychotic of the present invention. Water, gelatin, lactose, starches, magnesium stearate, talc, animal fats and oils, vegetable fats and oils, benzyl alcohol, gums, polyalkylene glycol, petroleum resins, coconut oil, lanolin, and all other carriers for medicines can be used as carriers for the antipsychotic of the present invention. Stabilizers, lubricants, emulsifying agents, and salts for changing an osmotic pressure or maintaining a suitable pH of the formulation can be appropriately used as adjuvants.

In respect of the safety of docosahexaenoic acid or derivatives thereof as active ingredients, the antipsychotic of the present invention is preferably used in the form of an aqueous solution in which the active ingredient is dispersed. In particular, the addition of a surfactant or emulsifying agent such as Tween 20, sucrose fatty ester, sorbitan fatty ester, lecithin, and monoglyceride is preferred.

Furthermore, for the treatment or prevention of psychosis such as schizophrenia, the antipsychotic of the present invention may contain other pharmaceutically active ingredients which can be suitably administered together with the antipsychotic of the present invention, such as other suitable antipsychotics, for example, haloperidol.

In the case of granules, subtilized granules, powders, tablets, or capsules, the antipsychotic of the present invention preferably contains from 5 to 80% by weight of the active ingredient. In the case of a solution, the antipsychotic of the present invention preferably contains from 1 to 30% by weight of the active ingredient. In the case of the injections for parenteral administration, the antipsychotic of the present invention preferably contains from 1 to 10% by weight of the active ingredient.

When the antipsychotic of the present invention is orally administered, the clinical dose of the active ingredient is preferably from 300 to 1800 mg per day for adult subjects, which can be varied depending on the age of the patients and severity of the condition to be treated. The antipsychotic of the present invention is preferably administered in the aforementioned daily dose either once a day, or twice or three times a day at suitable intervals.

When the antipsychotic of the present invention is used as an injection, it is preferably administered in doses of from 50 to 300 mg per application in terms of the active ingredient.

Docosahexaenoic acid and derivatives thereof utilized as the active ingredient of the anipsychotic drug of the present invention occur naturally in animals such as fish and also in plants. Furthermore, the presence of these compounds in the central nervous system of mammals including human beings has been confirmed and they are estimated for safety.

The present invention will be explained in more detail with reference to the following non-limiting working examples.

EXAMPLE 1

Method

It was confirmed in 1982 that PCP, a schizophrenia-like symptom inducing agent, was an antagonist of NMDA receptors, thus revealing the association of abnormal transmission of glutamic acid with this kind of schizophrenic diseases. Under the circumstances, the effects of docosahexaenoic acid on NMDA receptors of PCP were investigated.

The investigation was conducted by an electrophysiological procedure. More specifically, the brain of a 2-week-old rat was delivered and slices were prepared. Then, neurons were taken from the hippocampal CA1 region and used as samples. An electrophysiological test was conducted by a patch clamp method under fixed potential conditions.

Results

As shown in FIG. 1, the treatment of sample cells with 30 $\mu$M of NMDA caused an inward current of 300 pA at a holding potential of −50 mV. In subsequent treatments with 5 $\mu$M of PCP and 30 $\mu$M of NMDA, the current decreased by half. Upon a further subsequent treatment with 30 $\mu$M of docosahexaenoic acid (DHA), the current recovered to the same level as that prior to the blockage with PCP (FIG. 1A).

Figure 1D:
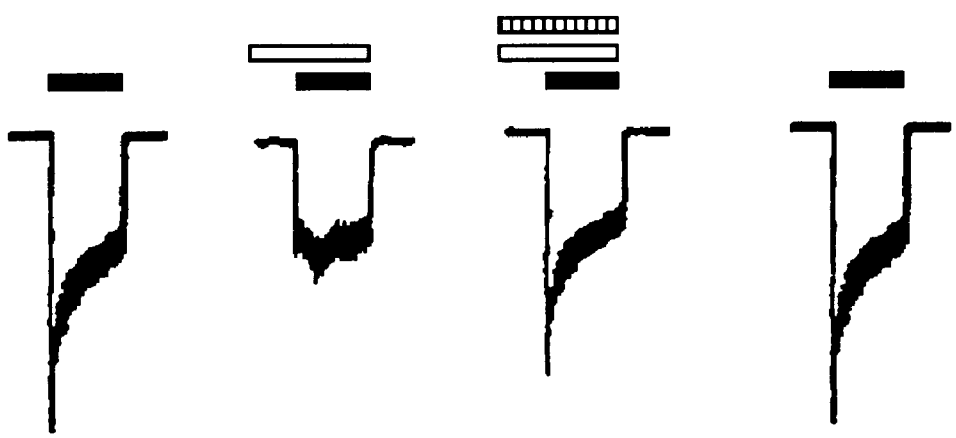

Similar effects were provided by treatments with 1 $\mu$M each of 14-hydroxy docosahexaenoic acid (14-HDHE) which is a lipoxygenase metabolite of docosahexaenoic acid (FIG. 1B), 7-hydroxy docosahexaenoic acid (7-HDHE, FIG. 1C), and 7,8-epoxy docosapentaenoic acid (7,8-EDP) which is a P450 dehydrogenase metabolite (Figure 1D). These results show that the action of PCP was attenuated with docosahexaenoic acid or metabolites thereof. Thus, it was suggested that docosahexaenoic acid and metabolites thereof have a potential to prevent or alleviate PCP-induced schizophrenia.

EXAMPLE 2

Method

Sixteen subjects aged from 35 to 60 were treated with either the antipsychotic of the present invention or a placebo. Eleven out of these sixteen subjects had been treated with chlorpromazine and haloperidol in the past. Eight subjects were treated with the antipsychotic of the present invention and the other eight were treated with the placebo.

Docosahexaenoic acid or placebo was orally administered to the subjects three times a day, each in a dose of 300 mg.

Results

After one-month administration of the antipsychotic of the present invention, six out of the eight treated subjects showed improvements in negative symptoms of schizophrenia. In contrast, the placebo group showed no marked improvements in those symptoms. The one-month administration caused neither primary side effects nor significant variations in biochemical blood and urine tests. Other findings were a reduced total cholesterol and an increased HDL-cholesterol but there was no significant differences in these values.

According to the present invention, an antipsychotic can be provided which is effective in treating or preventing psychosis and which is highly safe.

What is claimed is:

1. An antipsychotic comprising a lipoxygenase metabolite of docosahexaenoic acid or derivative thereof selected from the group consisting of 14-hydroxydocosahexaenoic acid, ethyl 14-hydroxydocosahexaenoate, 7-hydroxydocosahexaenoic acid or ethyl 7-hydroxydocosahexaenoate.

2. An antipsychotic comprising a P450 dehydrogenase metabolite of docosahexaenoic acid or derivative thereof selected from the group consisting of 7,8-epoxydocosapentaenoic acid or ethyl 7,8-epoxydocosapentaenoate.

3. A method for treating psychosis, comprising administering an effective dosage of at least one lipoxygenase metabolite of docosahexaenoic acid or derivative thereof.

4. The method according to claim 3, wherein the lipoxygenase metabolite or derivative thereof is selected from the group consisting of 14-hydroxydocosahexaenoic acid, ethyl 14-hydroxydocosahexaenoate, 7-hydroxydocosahexaenoic acid or ethyl 7-hydroxydocosahexaenoate.

5. A method for treating psychosis, comprising administering an effective dosage of at least one P450 dehydrogenase metabolite of docosahexaenoic acid or derivative thereof.

6. The method according to claim 5, wherein the P450 dehydrogenase metabolite or derivative thereof is selected from the group consisting of 7,8-epoxydocosapentaenoic acid or ethyl 7,8-epoxydocosapentaenoate.

7. A method for treating psychosis, comprising administering an effective dosage of a composition consisting essentially of a phospholipid or triglyceride of docosahexaenoic acid.

* * * * *

UNITED STATES PATENT AND TRADEMARK OFFICE
CERTIFICATE OF CORRECTION

PATENT NO.    : 6,306,907 B1
DATED         : October 23, 2001
INVENTOR(S)   : Masazumi Nishikawa et al.

It is certified that error appears in the above-identified patent and that said Letters Patent is hereby corrected as shown below:

<u>Title page,</u>
Item [73], Assignee, "Taiyo Fishery Co., Ltd., Tokyo (JP)" should read -- Maruha Corporation, Tokyo (JP) --

Signed and Sealed this

Twenty-first Day of January, 2003

JAMES E. ROGAN
*Director of the United States Patent and Trademark Office*